(12) United States Patent  (10) Patent No.: US 8,388,612 B2
Dunning et al.  (45) Date of Patent: Mar. 5, 2013

(54) TEMPERATURE MONITORING RETURN ELECTRODE

(75) Inventors: James E. Dunning, Lafayette, CO (US); Peter Gadsby, Broomfield, CO (US); David Gresback, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 1448 days.

(21) Appl. No.: 11/803,129

(22) Filed: May 11, 2007

(65) Prior Publication Data

US 2008/0281311 A1 Nov. 13, 2008

(51) Int. Cl.
*A61B 18/16* (2006.01)
(52) U.S. Cl. .......................................... 606/32
(58) Field of Classification Search .................. 600/372, 600/374, 382, 391, 392; 606/32, 34, 41, 606/42; 607/142, 152, 129, 101–102
See application file for complete search history.

(56) References Cited

U.S. PATENT DOCUMENTS

| | | | |
|---|---|---|---|
| 2,536,271 A | 1/1951 | Fransen et al. |
| 3,380,445 A | 4/1968 | Frasier |
| 3,534,306 A | 10/1970 | Watrous et al. |
| 3,543,760 A | 12/1970 | Bolduc |
| 3,642,008 A | 2/1972 | Bolduc |
| 3,683,923 A | 8/1972 | Anderson |
| 3,812,861 A | 5/1974 | Peters |
| 3,913,583 A | 10/1975 | Bross |
| 3,923,063 A | 12/1975 | Andrews et al. |
| 3,933,157 A | 1/1976 | Bjurwill et al. |
| 3,987,796 A | 10/1976 | Gonser |
| 4,067,342 A | 1/1978 | Burton |
| 4,092,985 A | 6/1978 | Kaufman |
| 4,094,320 A | 6/1978 | Newton et al. |
| 4,102,341 A | 7/1978 | Ikuno et al. |
| 4,114,622 A | 9/1978 | Gonser |
| 4,117,846 A | 10/1978 | Williams |
| 4,121,590 A | 10/1978 | Gonser |
| 4,126,137 A | 11/1978 | Archibald |
| 4,166,465 A | 9/1979 | Esty et al. |
| 4,188,927 A | 2/1980 | Harris |
| 4,200,104 A | 4/1980 | Harris |
| 4,200,105 A | 4/1980 | Gonser |
| 4,213,463 A | 7/1980 | Osenkarski |
| 4,231,372 A | 11/1980 | Newton |

(Continued)

FOREIGN PATENT DOCUMENTS

CA 1 219642 3/1987
DE 3206947 9/1983
(Continued)

OTHER PUBLICATIONS

International Search Report PCT/US2004/004196 dated Oct. 4, 2007.

(Continued)

*Primary Examiner* — Michael Peffley
*Assistant Examiner* — Ronald Hupczey, Jr.

(57) ABSTRACT

An electrosurgical return electrode includes a conductive pad including a patient-contacting surface configured to conduct electrosurgical energy, and a temperature sensing circuit coupled to the conductive pad. The temperature sensing circuit includes a plurality of switching elements connected in series, wherein each of the plurality of switching elements is configured to vary in impedance in response to temperature changes, such that an interrogation signal transmitted therethrough is indicative of the temperature change.

4 Claims, 7 Drawing Sheets

U.S. PATENT DOCUMENTS

| | | | |
|---|---|---|---|
| 4,237,887 A | 12/1980 | Gonser |
| 4,253,721 A | 3/1981 | Kaufman |
| 4,303,073 A | 12/1981 | Archibald |
| 4,304,235 A | 12/1981 | Kaufman |
| 4,331,149 A | 5/1982 | Gonser |
| 4,343,308 A | 8/1982 | Gross |
| 4,381,789 A | 5/1983 | Naser et al. |
| 4,384,582 A | 5/1983 | Watt |
| 4,387,714 A | 6/1983 | Geddes et al. |
| 4,393,584 A | 7/1983 | Bare et al. |
| 4,416,276 A | 11/1983 | Newton et al. |
| 4,416,277 A | 11/1983 | Newton et al. |
| 4,437,464 A | 3/1984 | Crow |
| 4,494,541 A | 1/1985 | Archibald |
| 4,643,193 A | 2/1987 | DeMarzo |
| 4,657,015 A | 4/1987 | Irnich |
| 4,658,819 A | 4/1987 | Harris et al. |
| 4,662,369 A | 5/1987 | Ensslin |
| 4,669,468 A | 6/1987 | Cartmell et al. |
| 4,699,146 A | 10/1987 | Sieverding |
| 4,722,761 A | 2/1988 | Cartmell et al. |
| 4,725,713 A | 2/1988 | Lehrke |
| 4,741,334 A | 5/1988 | Irnich |
| 4,745,918 A | 5/1988 | Feucht |
| 4,748,983 A | 6/1988 | Shigeta et al. |
| 4,750,482 A | 6/1988 | Sieverding |
| 4,754,757 A | 7/1988 | Feucht |
| 4,768,514 A | 9/1988 | DeMarzo |
| 4,770,173 A | 9/1988 | Feucht et al. |
| 4,788,977 A | 12/1988 | Farin et al. |
| 4,799,480 A | 1/1989 | Abraham et al. |
| 4,807,621 A | 2/1989 | Hagen et al. |
| 4,844,063 A | 7/1989 | Clark |
| 4,848,335 A | 7/1989 | Manes |
| 4,862,889 A | 9/1989 | Feucht |
| 4,873,974 A | 10/1989 | Hagen et al. |
| 4,895,169 A | 1/1990 | Heath |
| 4,942,313 A | 7/1990 | Kinzel |
| 4,947,846 A | 8/1990 | Kitagawa et al. |
| 4,955,381 A | 9/1990 | Way et al. |
| 4,961,047 A | 10/1990 | Carder |
| 4,969,885 A | 11/1990 | Farin |
| 5,000,753 A | 3/1991 | Hagen et al. |
| 5,004,425 A | 4/1991 | Hee |
| 5,010,896 A | 4/1991 | Westbrook |
| 5,038,796 A | 8/1991 | Axelgaard et al. |
| 5,042,981 A | 8/1991 | Gross |
| 5,061,914 A | 10/1991 | Busch et al. |
| 5,087,257 A | 2/1992 | Farin |
| 5,114,424 A | 5/1992 | Hagen et al. |
| 5,152,762 A | 10/1992 | McElhenney |
| 5,160,334 A | 11/1992 | Billings et al. |
| 5,196,008 A | 3/1993 | Kuenecke |
| 5,246,439 A | 9/1993 | Hebborn et al. |
| 5,271,417 A | 12/1993 | Swanson et al. |
| 5,276,079 A | 1/1994 | Duan et al. |
| 5,286,255 A | 2/1994 | Weber |
| 5,312,401 A | 5/1994 | Newton et al. |
| 5,336,255 A | 8/1994 | Kanare et al. |
| 5,352,315 A | 10/1994 | Carrier et al. |
| 5,362,420 A | 11/1994 | Itoh et al. |
| 5,370,645 A | 12/1994 | Klicek et al. |
| 5,385,679 A | 1/1995 | Uy et al. |
| 5,388,490 A | 2/1995 | Buck |
| 5,389,376 A | 2/1995 | Duan et al. |
| 5,390,382 A | 2/1995 | Hannant et al. |
| 5,409,966 A | 4/1995 | Duan et al. |
| 5,447,513 A | 9/1995 | Davison et al. |
| 5,449,365 A | 9/1995 | Green et al. |
| 5,452,725 A | 9/1995 | Martenson |
| 5,480,399 A | 1/1996 | Hebborn |
| 5,496,312 A | 3/1996 | Klicek |
| 5,496,363 A | 3/1996 | Burgio et al. |
| 5,520,180 A | 5/1996 | Uy et al. |
| 5,536,446 A | 7/1996 | Uy et al. |
| 5,540,684 A | 7/1996 | Hassler, Jr. |
| 5,599,347 A | 2/1997 | Hart et al. |
| 5,601,618 A | 2/1997 | James |
| 5,611,709 A | 3/1997 | McAnulty |
| 5,632,280 A | 5/1997 | Leyde et al. |
| 5,643,319 A | 7/1997 | Green et al. |
| 5,660,892 A | 8/1997 | Robbins et al. |
| 5,670,557 A | 9/1997 | Dietz et al. |
| 5,674,561 A | 10/1997 | Dietz et al. |
| 5,678,545 A | 10/1997 | Stratbucker |
| 5,688,269 A | 11/1997 | Newton et al. |
| 5,695,494 A | 12/1997 | Becker |
| 5,707,369 A | 1/1998 | Vaitekunas et al. |
| 5,718,719 A | 2/1998 | Clare et al. |
| 5,720,744 A | 2/1998 | Eggleston et al. |
| 5,766,165 A | 6/1998 | Gentelia et al. |
| 5,779,632 A | 7/1998 | Dietz et al. |
| 5,797,902 A | 8/1998 | Netherly |
| 5,800,426 A | 9/1998 | Taki et al. |
| 5,817,091 A | 10/1998 | Nardella et al. |
| 5,830,212 A | 11/1998 | Cartmell et al. |
| 5,836,942 A | 11/1998 | Netherly et al. |
| 5,846,558 A | 12/1998 | Nielsen et al. |
| 5,853,750 A | 12/1998 | Dietz et al. |
| 5,868,742 A | 2/1999 | Manes et al. |
| 5,924,983 A | 7/1999 | Takaki et al. |
| 5,947,961 A | 9/1999 | Netherly |
| 5,952,398 A | 9/1999 | Dietz et al. |
| 5,971,981 A | 10/1999 | Hill et al. |
| 5,976,128 A | 11/1999 | Schilling et al. |
| 5,985,990 A | 11/1999 | Kantner et al. |
| 5,999,061 A | 12/1999 | Pope et al. |
| 6,007,532 A | 12/1999 | Netherly |
| 6,010,054 A | 1/2000 | Johnson et al. |
| 6,030,381 A | 2/2000 | Jones et al. |
| 6,032,063 A | 2/2000 | Hoar et al. |
| 6,039,732 A | 3/2000 | Ichikawa et al. |
| 6,053,910 A | 4/2000 | Fleenor |
| RE36,720 E | 5/2000 | Green et al. |
| 6,059,778 A | 5/2000 | Sherman |
| 6,063,075 A | 5/2000 | Mihori |
| 6,083,221 A | 7/2000 | Fleenor et al. |
| 6,086,249 A | 7/2000 | Urich |
| 6,121,508 A | 9/2000 | Bischof et al. |
| 6,135,953 A | 10/2000 | Carim |
| 6,171,304 B1 | 1/2001 | Netherly et al. |
| 6,200,314 B1 | 3/2001 | Sherman |
| 6,203,541 B1 | 3/2001 | Keppel |
| 6,214,000 B1 | 4/2001 | Fleenor et al. |
| 6,232,366 B1 | 5/2001 | Wang et al. |
| 6,240,323 B1 | 5/2001 | Calenzo, Sr. et al. |
| 6,258,085 B1 | 7/2001 | Eggleston |
| 6,275,786 B1 | 8/2001 | Daners |
| 6,301,500 B1 | 10/2001 | Van Herk et al. |
| 6,310,611 B1 | 10/2001 | Caldwell |
| 6,347,246 B1 | 2/2002 | Perrault et al. |
| 6,350,264 B1 | 2/2002 | Hooven |
| 6,357,089 B1 | 3/2002 | Koguchi et al. |
| 6,358,245 B1 | 3/2002 | Edwards et al. |
| 6,379,161 B1 | 4/2002 | Ma |
| 6,409,722 B1 | 6/2002 | Hoey et al. |
| 6,413,255 B1 | 7/2002 | Stern |
| 6,415,170 B1 | 7/2002 | Loutis et al. |
| 6,454,764 B1 | 9/2002 | Fleenor et al. |
| 6,488,678 B2 | 12/2002 | Sherman |
| 6,537,272 B2 | 3/2003 | Christopherson et al. |
| 6,544,258 B2 | 4/2003 | Fleenor et al. |
| 6,546,270 B1 | 4/2003 | Goldin et al. |
| 6,565,559 B2 | 5/2003 | Eggleston |
| 6,569,160 B1 | 5/2003 | Goldin et al. |
| 6,582,424 B2 | 6/2003 | Fleenor et al. |
| 6,666,859 B1 | 12/2003 | Fleenor et al. |
| 6,669,073 B2 | 12/2003 | Milliman et al. |
| 6,736,810 B2 | 5/2004 | Hoey et al. |
| 6,796,828 B2 | 9/2004 | Ehr et al. |
| 6,799,063 B2 | 9/2004 | Carson |
| 6,830,569 B2 | 12/2004 | Thompson et al. |
| 6,849,073 B2 | 2/2005 | Hoey et al. |
| 6,860,881 B2 | 3/2005 | Sturm |
| 6,875,210 B2 | 4/2005 | Reflio et al. |
| 6,892,086 B2 | 5/2005 | Russell |
| 6,905,497 B2 | 6/2005 | Truckai et al. |

| | | |
|---|---|---|
| 6,939,344 B2 | 9/2005 | Kreindel |
| 6,948,503 B2 | 9/2005 | Refior et al. |
| 6,953,139 B2 | 10/2005 | Milliman et al. |
| 6,959,852 B2 | 11/2005 | Shelton, IV et al. |
| 6,997,735 B2 | 2/2006 | Ehr et al. |
| 7,025,765 B2 | 4/2006 | Balbierz et al. |
| 7,128,253 B2 | 10/2006 | Mastri et al. |
| 7,143,926 B2 | 12/2006 | Shelton, IV et al. |
| 7,160,293 B2 | 1/2007 | Sturm et al. |
| 7,166,102 B2 | 1/2007 | Fleenor et al. |
| 7,169,144 B2 | 1/2007 | Hoey et al. |
| 7,169,145 B2 | 1/2007 | Isaacson et al. |
| 7,182,604 B2 | 2/2007 | Ehr et al. |
| 7,220,260 B2 | 5/2007 | Fleming et al. |
| 7,229,307 B2 | 6/2007 | Ehr et al. |
| 7,258,262 B2 | 8/2007 | Mastri et al. |
| 7,267,675 B2 | 9/2007 | Stern et al. |
| 7,278,562 B2 | 10/2007 | Mastri et al. |
| 7,303,107 B2 | 12/2007 | Milliman et al. |
| 7,308,998 B2 | 12/2007 | Mastri et al. |
| 7,311,560 B2 | 12/2007 | Ehr et al. |
| 7,357,287 B2 | 4/2008 | Shelton, IV et al. |
| 7,380,695 B2 | 6/2008 | Doll et al. |
| 7,422,589 B2 | 9/2008 | Newton et al. |
| 7,473,145 B2 | 1/2009 | Ehr et al. |
| 7,736,357 B2 * | 6/2010 | Lee et al. .................. 606/34 |
| 7,909,819 B2 * | 3/2011 | Falkenstein et al. ........... 606/32 |
| 2003/0139741 A1 | 7/2003 | Goble et al. |
| 2004/0150504 A1 | 8/2004 | Nicholson |
| 2005/0021022 A1 | 1/2005 | Sturm et al. |
| 2005/0079752 A1 | 4/2005 | Ehr et al. |
| 2005/0085806 A1 | 4/2005 | Auge, II et al. |
| 2005/0101947 A1 * | 5/2005 | Jarrard et al. .................. 606/35 |
| 2005/0251130 A1 | 11/2005 | Boveja et al. |
| 2006/0030195 A1 | 2/2006 | Ehr et al. |
| 2006/0041251 A1 | 2/2006 | Odell et al. |
| 2006/0041252 A1 | 2/2006 | Odell et al. |
| 2006/0041253 A1 | 2/2006 | Newton et al. |
| 2006/0074411 A1 | 4/2006 | Carmel et al. |
| 2006/0079872 A1 | 4/2006 | Eggleston |
| 2006/0173250 A1 | 8/2006 | Nessler |
| 2006/0217742 A1 | 9/2006 | Messerly et al. |
| 2006/0224150 A1 | 10/2006 | Arts et al. |
| 2007/0049914 A1 | 3/2007 | Eggleston |
| 2007/0049916 A1 | 3/2007 | Isaacson et al. |
| 2007/0049919 A1 | 3/2007 | Lee, Jr. et al. |
| 2007/0073284 A1 | 3/2007 | Sturm |
| 2007/0074719 A1 | 4/2007 | Danek et al. |
| 2007/0161979 A1 | 7/2007 | McPherson |
| 2007/0167942 A1 | 7/2007 | Rick |
| 2007/0203481 A1 | 8/2007 | Gregg et al. |
| 2007/0244478 A1 | 10/2007 | Bahney |
| 2008/0009846 A1 | 1/2008 | Ward |
| 2008/0033276 A1 | 2/2008 | Ehr et al. |
| 2008/0058792 A1 * | 3/2008 | Falkenstein et al. ........... 606/32 |
| 2008/0083806 A1 | 4/2008 | Scirica |
| 2008/0083813 A1 | 4/2008 | Zemlok et al. |
| 2008/0249520 A1 | 10/2008 | Dunning et al. |
| 2008/0249524 A1 | 10/2008 | Dunning |
| 2008/0281309 A1 | 11/2008 | Dunning et al. |
| 2008/0281310 A1 | 11/2008 | Dunning et al. |
| 2008/0281311 A1 | 11/2008 | Dunning et al. |
| 2009/0036884 A1 | 2/2009 | Gregg et al. |
| 2009/0036885 A1 | 2/2009 | Gregg |

FOREIGN PATENT DOCUMENTS

| | | |
|---|---|---|
| DE | 3544443 | 6/1987 |
| DE | 42 38 263 A1 | 5/1993 |
| DE | 4231236 | 3/1994 |
| DE | 197 17 411 A1 | 11/1998 |
| DE | 198 01 173 | 7/1999 |
| DE | 103 28 514 | 6/2003 |
| DE | 102004010940 | 9/2005 |
| EP | 0262888 | 4/1988 |
| EP | 390937 | 10/1990 |
| EP | 836868 | 4/1998 |
| EP | 0 930 048 | 7/1999 |
| EP | 1 051 949 | 11/2000 |
| EP | 1076350 | 2/2001 |
| EP | 1 468 653 | 10/2004 |
| EP | 1 645 236 | 4/2006 |
| EP | 1707151 * | 4/2006 |
| EP | 1707151 | 10/2006 |
| EP | 1 808 144 | 7/2007 |
| EP | 1902684 | 3/2008 |
| FR | 2276027 | 6/1974 |
| FR | 2516782 | 5/1983 |
| GB | 2 054 382 | 2/1981 |
| GB | 2374532 | 10/2002 |
| WO | WO 96/19152 | 6/1996 |
| WO | WO 97/37719 | 10/1997 |
| WO | WO 98/18395 | 5/1998 |
| WO | WO 98/53751 | 12/1998 |
| WO | WO 99/09899 | 3/1999 |
| WO | WO 99/11187 | 3/1999 |
| WO | WO 00/06246 | 2/2000 |
| WO | WO 00/32122 | 6/2000 |
| WO | WO 00/53113 | 9/2000 |
| WO | WO 00/65993 | 11/2000 |
| WO | WO 01/87175 | 11/2001 |
| WO | WO 02/058579 | 8/2002 |
| WO | WO 02/060526 | 8/2002 |
| WO | WO 02/099442 | 12/2002 |
| WO | WO 03/094766 | 11/2003 |
| WO | WO 2004/028385 | 4/2004 |
| WO | WO 2004/074854 | 9/2004 |
| WO | WO 2005/048809 | 6/2005 |
| WO | WO 2005/087124 | 9/2005 |
| WO | WO 2005/099606 | 10/2005 |
| WO | WO 2005099606 | 10/2005 |
| WO | WO 2005/110263 | 11/2005 |
| WO | WO 2005/115262 | 12/2005 |
| WO | WO 2008/009385 | 1/2008 |

OTHER PUBLICATIONS

International Search Report EP06006961.4 dated Oct. 5, 2007.
International Search Report EP07000885.9 dated May 2, 2007.
International Search Report EP07007783.9 dated Aug. 6, 2007.
International Search Report EP06018206.0 dated Oct. 13, 2006.
International Search Report EP07000567.3 dated Dec. 3, 2008.
International Search Report EP08006731 dated Jul. 14, 2008.
International Search Report EP08006735.8 dated Jan. 8, 2009.
International Search Report EP08008510.3 dated Oct. 27, 2008.
International Search Report EP08013758.1 dated Nov. 20, 2008.
International Search Report EP08013760.7 dated Nov. 20, 2008.
International Search Report EP08155779-partial dated Sep. 8, 2008.
International Search Report EP08155779 dated Jan. 23, 2009.
International Search Report EP09152032 dated Jun. 17, 2009.
International Search Report EP09152130.2 dated Apr. 6, 2009.
International Search Report EP 05021944.3 dated Jan. 25, 2006.
International Search Report EP 05002027.0 dated May 12, 2005.
International Search Report EP 06006961 dated Aug. 3, 2006.
International Search Report EP 07000885.9 dated May 15, 2007.
Boyles, Walt; "Instrumentation Reference Book", 2002; Butterworth-Heinemann ; 262-264.
International Search Report EP06023756.7 dated Feb. 21, 2008.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.

* cited by examiner

TEMPERATURE MONITORING RETURN ELECTRODE

BACKGROUND

1. Technical Field

The present disclosure relates to electrosurgical apparatuses, systems and methods. More particularly, the present disclosure is directed to electrosurgical systems utilizing one or more return electrodes configured to monitor temperature.

2. Background of Related Art

Energy-based tissue treatment is well known in the art. Various types of energy (e.g., electrical, ultrasonic, microwave, cryo, heat, laser, etc.) may be applied to tissue to achieve a desired surgical result. Electrosurgery typically involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the user and applied to the tissue to be treated. The patient return electrodes are typically in the form of pads adhesively adhered to the patient and are placed remotely from the active electrode to carry the current back to the generator.

The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle (i.e., the percentage of time the generator is on).

The first types of return electrodes were in the form of large metal plates covered with conductive jelly. Later, adhesive electrodes were developed with a single metal foil covered with conductive jelly or conductive adhesive. However, one problem with these adhesive electrodes was that if a portion peeled from the patient, the contact area of the electrode with the patient decreased, thereby increasing the current density at the adhered portion and, in turn, increasing the heating at the tissue. This risked burning the patient in the area under the adhered portion of the return electrode if the tissue was heated beyond the point where circulation of blood could cool the skin.

To address this problem various return electrodes and hardware circuits, generically called Return Electrode Contact Quality Monitors (RECQMs), were developed. Such systems relied on measuring impedance at the return electrode to calculate a variety of tissue and/or electrode properties. These systems were only configured to measure changes in impedance of the return electrodes to detect peeling.

SUMMARY

The present disclosure relates to electrosurgical return electrodes. Disclosure provides for an electrosurgical return electrode pad having various mechanisms and/or circuits adapted to prevent tissue damage to the patient. The return electrode pad monitors temperature and upon the temperature reaching a predetermined threshold the pad activates safety circuits and/or alarms. Further, a modular smart return electrode is disclosed having a disposable portion and a detachable portion including sensor and/or control circuits.

According to one aspect of the present disclosure, an electrosurgical return electrode is provided. The return electrode includes a first and second flexible conductive material layers, wherein impedance of the first and second conductive material layers in continuously monitored and a material layer disposed between the first and second conductive material layers. The material layer is transmitionable between a solid state and a non-solid state, the material layer is also configured to melt upon an increase in temperature beyond a predetermined threshold, thereby increasing conductivity between the first and second conductive material layer.

According to a further aspect of the present disclosure, an electrosurgical return electrode is disclosed. The return electrode includes a return electrode pad having a patient-contacting surface configured to conduct electrosurgical energy. The return electrode also includes a material layer disposed on the return electrode pad. The material layer includes at least one switching element having at least one switch component formed from a shape memory material that transmissions from an austensitic state to a martensitic state upon a change in temperature to actuate at least one switch component of the at least one switching element.

According to another embodiment of the present disclosure, an electrosurgical return electrode is disclosed. The return electrode includes a return electrode pad having a patient-contacting surface configured to conduct electrosurgical energy and a ferromagnetic material layer disposed on the return electrode pad. The ferromagnetic material layer includes a magnetic field and at least one temperature sensing switch, the ferromagnetic material layer is configured to lose a magnetic flux at a predetermined temperature threshold thereby actuating the at least one temperature sensing switch.

According to a further embodiment of the present disclosure an electrosurgical return electrode is disclosed. The return electrode includes a conductive pad including a patient-contacting surface configured to conduct electrosurgical energy and a temperature sensing circuit coupled to the conductive pad. The temperature sensing circuit includes a plurality of switching elements connected in series, wherein each of the plurality of switching elements is configured to vary in impedance in response to temperature changes. An interrogation signal is transmitted therethrough measures impedance and is indicative of the temperature change.

An electrosurgical return electrode is also contemplated by the present disclosure. The return electrode includes a conductive pad including a patient-contacting surface configured to conduct electrosurgical energy and a temperature sensing circuit coupled to the conductive pad. The temperature sensing circuit includes a thermocouple matrix having a first plurality of metallic wires and a second plurality of metallic wires intersecting at a plurality of junctions, wherein each of the junctions is interrogated to obtain a temperature measurement.

According to another embodiment of the present disclosure, a modular electrosurgical return electrode is disclosed. The return electrode includes a disposable portion having a patient-contacting surface configured to conduct electrosurgical energy and a detachable substrate having a sensor circuit configured to monitor at least one of a return electrode pad property and a tissue property to generate sensor data. The detachable substrate is configured to couple to the disposable portion.

According to a further embodiment of the present disclosure, an electrosurgical return electrode is disclosed. The return electrode includes a conductive pad including a patient-contacting surface configured to conduct electrosurgical energy and a temperature sensing circuit coupled to the conductive pad. The temperature sensing circuit includes at least one transistor coupled to a multiplexer, the at least one transistor having a predetermined forward voltage drop that is indicative of temperature of the conductive pad.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
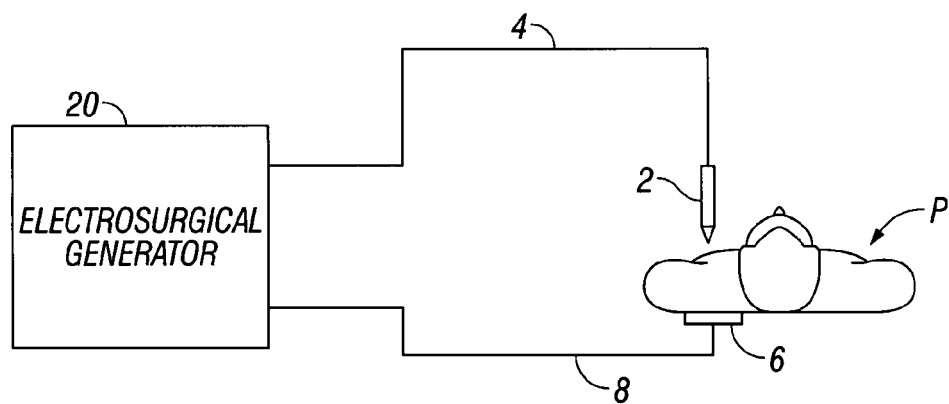
FIG. 1 is a schematic block diagram of an electrosurgical system according to the present disclosure.

FIG. 1 is a schematic illustration of an electrosurgical system according to one embodiment of the present disclosure. The system includes an electrosurgical instrument 2 having one or more electrodes for treating tissue of a patient P. The instrument 2 is a monopolar instrument including one or more active electrodes (e.g., electrosurgical cutting probe, ablation electrode(s), etc.). Electrosurgical RF energy is supplied to the instrument 2 by a generator 20 via an electrosurgical cable 4, which is connected to an active output terminal, allowing the instrument 2 to coagulate, ablate and/or otherwise treat tissue. The energy is returned to the generator 20 through a return electrode 6 via a return cable 8. The system may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage.

The generator 20 includes input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform, and other parameters to achieve the desired waveform suitable for a particular task (e.g., coagulating, tissue sealing, intensity setting, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

Figure 2:
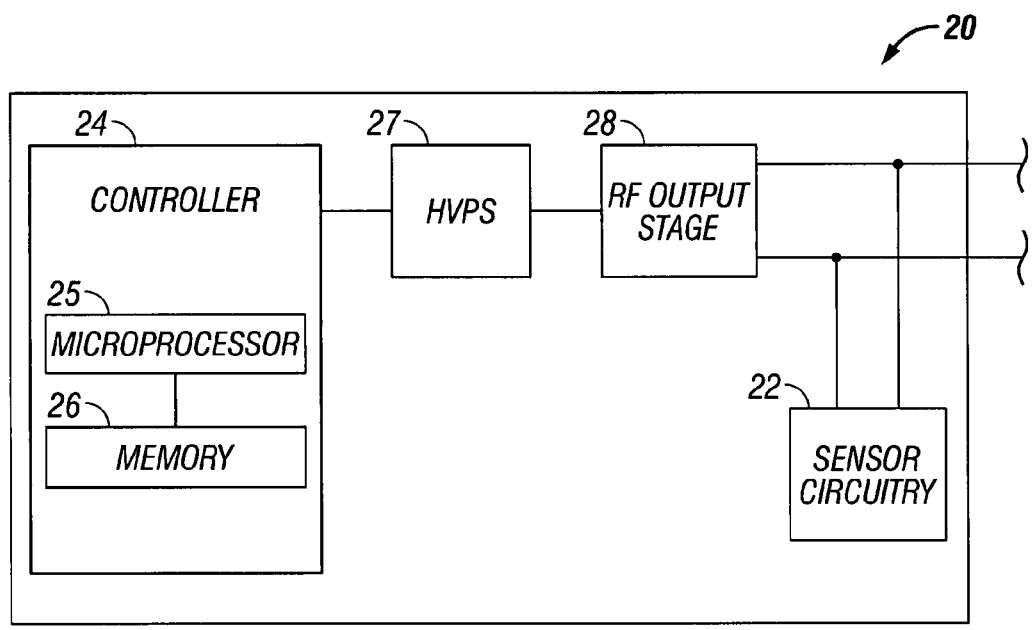
FIG. 2 is a schematic block diagram of a generator according to one embodiment of the present disclosure.

FIG. 2 shows a schematic block diagram of the generator 20 having a controller 24, a high voltage DC power supply 27 ("HVPS") and an RF output stage 28. The HVPS 27 provides high voltage DC power to an RF output stage 28, which then converts high voltage DC power into RF energy and delivers the RF energy to the active electrode. In particular, the RF output stage 28 generates sinusoidal waveforms of high RF energy. The RF output stage 28 is configured to generate a plurality of waveforms having various duty cycles, peak voltages, crest factors, and other suitable parameters. Certain types of waveforms are suitable for specific electrosurgical modes. For instance, the RF output stage 28 generates a 100% duty cycle sinusoidal waveform in cut mode, which is best suited for ablating, fusing and dissecting tissue, and a 1-25% duty cycle waveform in coagulation mode, which is best used for cauterizing tissue to stop bleeding.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RF output stage 28 that allows the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme is a feedback control loop wherein sensor circuit 22, which may include a plurality of sensors measuring a variety of tissue and energy properties (e.g., tissue impedance, tissue temperature, output current and/or voltage, etc.), provides feedback to the controller 24. Such sensors are within the purview of those skilled in the art. The controller 24 then signals the HVPS 27 and/or RF output stage 28, which then adjust DC and/or RF power supply, respectively. The controller 24 also receives input signals from the input controls of the generator 20 or the instrument 2. The controller 24 utilizes the input signals to adjust power outputted by the generator 20 and/or performs other control functions thereon.

Figure 3:
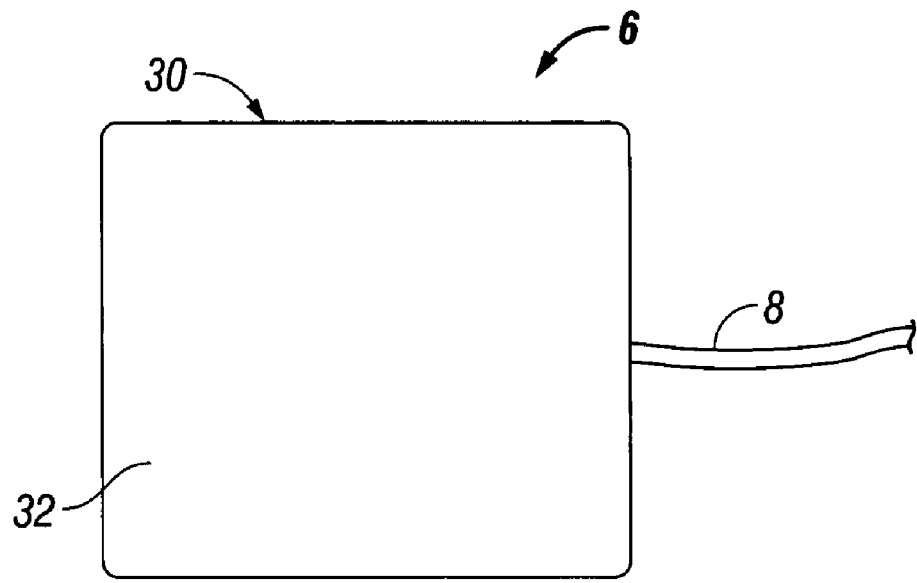
FIG. 3 is a top view of the electrosurgical return electrode of the monopolar electrosurgical system of FIG. 1.
Figure 4:
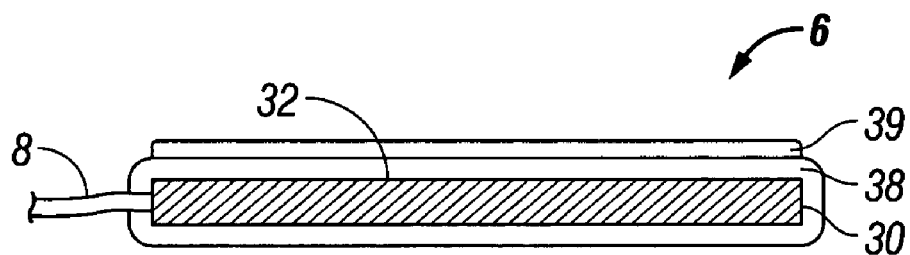
FIG. 4 is a cross-sectional side view of an electrosurgical return electrode having a positive temperature coefficient (PTC) material and adhesive material layers.

FIGS. 3 and 4 illustrate various embodiments of the return electrode 6 for use in monopolar electrosurgery. The return electrode 6 includes a return electrode pad 30 having a top surface and a patient-contacting surface 32 configured to receive current during monopolar electrosurgery. The patient-contacting surface 32 is made from a suitable conductive material such as metallic foil. While FIG. 3 depicts the return electrode 6 in a general rectangular shape, it is within the scope of the disclosure for the return electrode 6 to have any suitable regular or irregular shape.

Referring to FIG. 4, another embodiment of the return electrode 6 is shown, wherein the return electrode pad 30 includes a positive temperature coefficient (PTC) material layer 38 deposited thereon. The PTC material 38 can be made of, inter alia, a polymer/carbon-based material, a cermet-based material, a polymer material, a ceramic material, a dielectric material, or any combinations thereof. The PTC material layer 38 acts to distribute the temperature created by the current over the surface of the electrosurgical return electrode 6, which minimizes the risk of a patient burn. The PTC material of the layer 38 may be replaced by a negative temperature coefficient material. These materials change resistance dramatically when heated, allowing for monitoring of impedance to detect a rise in temperature, or automatic changes in localized current densities, thereby reducing localized heating.

The return electrode 6 further includes an adhesive material layer 39 on the patient-contacting surface 32. The adhesive material can be, but is not limited to, a polyhesive adhesive, a Z-axis adhesive, a water-insoluble, hydrophilic, pressure-sensitive adhesive, or any combinations thereof, such as POLYHESIVE™ adhesive manufactured by Valleylab of Boulder, Colo. The adhesive may be conductive and/or dielectric. The adhesive material layer 39 ensures an optimal surface contact area between the electrosurgical return electrode 6 and the patient "P," which limits the possibility of a patient burn. In an embodiment where PTC material layer 38 is not utilized, the adhesive material layer 39 may be deposited directly onto the patient-contacting surface 32.

Figure 5:
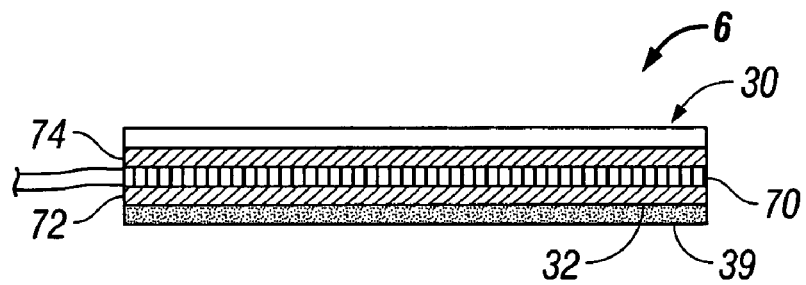
FIG. 5 is a cross-sectional side view of an electrosurgical return electrode having a material layer according to the present disclosure.

Referring to FIG. 5, another embodiment of the return electrode 6 is shown, wherein the return electrode pad 30 includes first and second foil layers 72 and 74, respectively, and a material layer 70 disposed therebetween. The return electrode 6 also includes the adhesive material layer 39 on the patient-contacting surface 32. The foil layers 72 and 74 are made from a suitable conductive material (e.g., metal) adapted to conduct the electrosurgical energy from the surgical site to the generator 20. The material layer 70 acts as a dielectric material and separates the foil layers 72 and 74 from each other by a predetermined distance (e.g., thickness of the material layer 70) thereby isolating the foil layers 72 and 74 and reducing the overall conductivity of the return electrode pad 30.

The material layer 70 is formed from a material that changes from a solid state to a non-solid state (e.g., liquid) at a predetermined temperature such as wax, temperature sensitive gel, jelly, plastic, various fats, low molecular weight organic compounds, polymer hydrogel and the like. The material of the material layer 70 has a melting point that approximately coincides with the maximum safe temperature—the temperature above which tissue damage starts to occur. A maximum safe temperature may be from about 40° C. to about 45° C. During normal operating temperatures (e.g., room temperature of about 20° C., body surface temperature of approximately 37° C.) the material layer 70 is in solid state but is flexible enough to allow for maximum conformity of the return electrode pad 30 to the patient.

When the return electrode pad 30 reaches the maximum safe temperature, the material layer 70 begins melting and undergoes a transmission from the solid state to a liquid state. As a result, the foil layers 72 and 74 come into electrical contact thereby increasing conduction therebetween. During operation, the impedance of the foil layers 72 and 74 is monitored. With increased conduction between the foil layers 72 and 74 impedance of the return electrode 30 drops. Monitoring the drop in impedance of the return electrode pad 30 allows the generator 20 to provide a temperature increase warning and/or adjust RF energy supply (e.g., shut off).

In another embodiment, when the material layer 70 is in a solid state, it provides an electrical interface between foil layers 72 and 74. When the material layer 70 melts, it would then increase resistance between foil layers 72 and 74 or break the electrical contact between foil layers 72 and 74. This change, in turn, could be utilized to provide a temperature increase warning and/or adjust RF energy supply (e.g., shut off). In still other embodiments, depending on the type of material used for material layer 70, the dielectric properties of material layer 70 could change with temperature, thus changing the value of capacitance between foil layers 72 and 74.

Figure 6A:
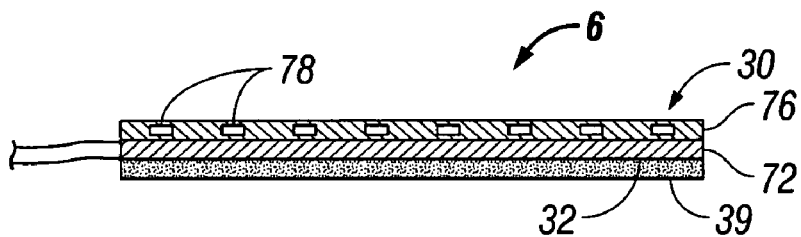
FIGS. 6A-C show an electrosurgical return electrode having a shape memory material layer according to the present disclosure.
Figure 6B:
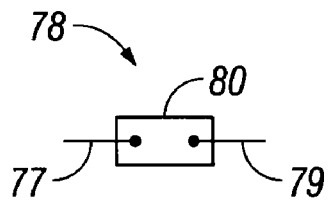
Figure 6C:
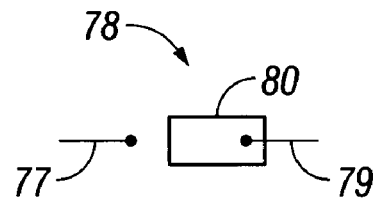

Referring to FIGS. 6A-C, another embodiment of the return electrode 6 is shown, wherein a shape memory material layer 76 is disposed on top of the return electrode pad 30 (e.g., the foil layer 72). The shape memory material layer 76 may be formed from a suitable shape memory alloy including shape memory metals such as nitinol, flexinol and the like. Shape memory materials change conformation (e.g., shape) at predetermined temperatures. The temperature at which the shape memory material reverts to its conformation is controlled by varying the ratio of shape memory materials of the alloy. The shape memory material of the layer 76 is configured to change shape at or around a maximum safe temperature, which may be from about 40° C. to about 45° C.

More particularly, shape memory alloys (SMAs) are a family of alloys having anthropomorphic qualities of memory and trainability. SMAs have been applied to such items as actuators for control systems, steerable catheters and clamps. One of the most common SMAs is Nitinol, which can retain shape memories for two different physical configurations and changes shape as a function of temperature Recently, other SMAs have been developed based on copper, zinc and aluminum and have similar shape memory retaining features.

SMAs undergo a crystalline phase transmission upon applied temperature and/or stress variations. A particularly useful attribute of SMAs is that after it is deformed by temperature/stress, it can completely recover its original shape on being returned to the original temperature. The ability of an alloy to possess shape memory is a result of the fact that the alloy undergoes a reversible transformation from an austensitic state to a martensitic state with a change in temperature/stress. This transformation is referred to as a thermoelastic martensitic transformation.

Under normal conditions, the thermoelastic martensitic transformation occurs over a temperature range, which varies with the composition of the alloy, itself, and the type of thermal-mechanical processing by which it was manufactured. In other words, the temperature at which a shape is "memorized" by an SMA is a function of the temperature at which the martensite and austenite crystals form in that particular alloy. For example, Nitinol alloys can be fabricated so that the shape memory effect may occur over a wide range of temperatures, e.g., −270° to +100° Celsius.

Many SMAs are also known to display stress-induced martensite (SIM) which occurs when the alloy is deformed from its original austenitic state to a martensitic state by subjecting the alloy to a stress condition.

The shape memory material layer 76 is constructed as an array of switching elements 78 as shown in FIGS. 6B-C. The switching elements 78 may be disposed on a suitable flex circuit (not explicitly shown) such as a flexible holding substrate 48 shown in FIG. 8B manufactured from a suitable substrate. The current flow to the switching elements 78 is provided by a power source (not explicitly shown), such as a low voltage DC power source (e.g., battery, AC/DC transformer, power source 50 of FIG. 8A etc.). The switching elements 78 include first and second switch components 77 and 79 that are formed from the shape memory material of the layer 76. The switch components 77 and 79 form a circuit around a connector 80, which may be a portion of the foil layer 76, flex circuit or any conducting strip of metal.

Upon a change in temperature, the SMA of the material layer 76 transmissions from an austenitic state to a martensitic state to actuate one or more of the switch components 77 and 79 of the switching element 78. More specifically, at normal operating temperatures (e.g., up to 40° C.), the first and second switch components 77 and 79 are in first configuration in relation to the connector 78. In the first configuration, the switch components 77 and 79 are arranged in a closed circuit, when the first and second components 77 and 79 are in contact with the connector 78, in which case in the second configuration the switch components 77 and 79 conform to create an open circuit. When the temperature changes due to over heating of the return electrode pad 30, the switch components 77 and 79, change to the second configuration, since the components are formed from a shape memory material. The first configuration may also be an open circuit configuration, and hence, in the second configuration, the switch components 77 and 79 are adapted to deform into a closed circuit configuration.

During operation, a low DC voltage signal (e.g., from DC power source) is passed through the switching elements 78 to determine the state thereof, e.g., whether the circuit is open or closed. When switching from the first to the second configuration occurs, the change in status of the switching elements 78 is indicative of a temperature increase above the maximum safe temperature. The status change is transmitted to the generator 20, wherein an alarm is generated or an adjustment to the RF supply is made.

Figure 7:
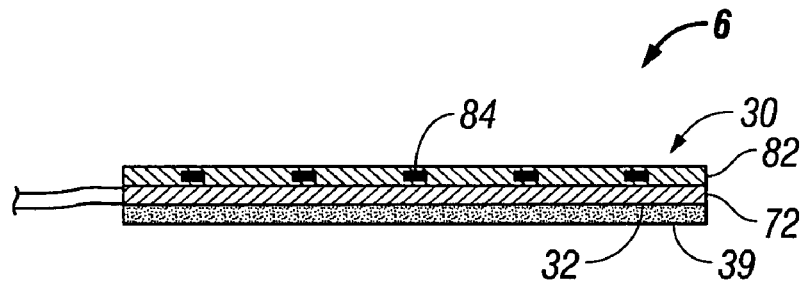
FIG. 7 is a cross-sectional side view of an electrosurgical return electrode having a ferromagnetic material layer according to the present disclosure.

FIG. 7 shows an embodiment of the return electrode 6 including a ferromagnetic material layer 82 being disposed on top of the return electrode pad 30 (e.g., the foil layer 72). The ferromagnetic material (e.g., liquid) exhibits spontaneous magnetization below a specific temperature point, the so-called Curie temperature. Above this temperature, the ferromagnetic material ceases to spontaneously exhibit magnetization. A ferromagnetic material that has a Curie temperature at or about a maximum safe temperature (e.g., 45° C.) such as manganese arsenic may be used, such that when temperature increases beyond the maximum safe temperature, the ferromagnetic material loses the magnetic field. The termination of the magnetic field is used as an activation mechanism for actuating one or more temperature sensing switches 84. The temperature sensing switches 84 may be magnetic field activatable switches, such as reed switches.

Figure 8A:
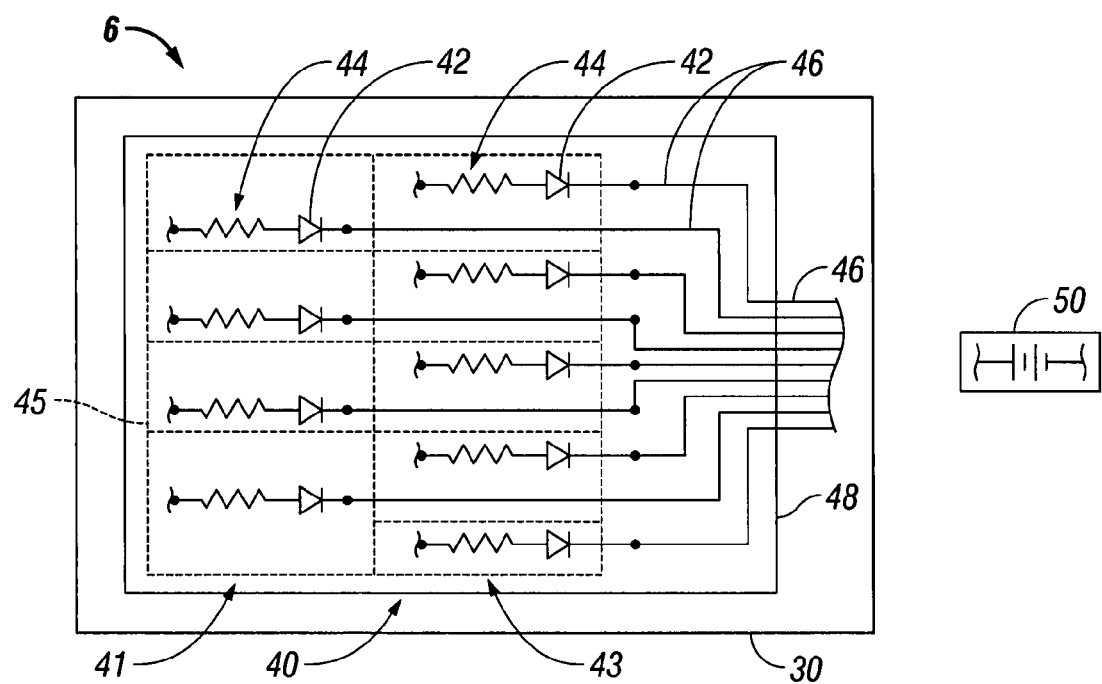
FIGS. 8A-C illustrate one embodiment of an electrosurgical return electrode having a temperature sensing circuit according to the present disclosure.
Figure 8B:
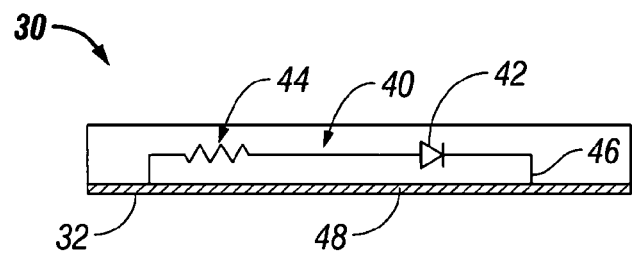

The temperature sensing switches 84 may be disposed on a flex circuit (not explicitly shown), such as a flexible holding substrate 48 shown in FIG. 8B manufactured from a suitable substrate. The current flow to the temperature sensing switches 84 is provided by a power source (not explicitly shown), such as a low voltage DC power source (e.g., battery, AC/DC transformer, power source 50 of FIG. 8A etc.).

The temperature sensing switches 84 are configured to remain open when the magnetic field is active (e.g., temperature of the return electrode pad 6 is below the maximum safe temperature) and close once the field terminates. The temperature sensing switches 84 may be substituted by magnetic field sensors (not explicitly shown) that are configured to measure changes in the magnetic field generated by the ferromagnetic material layer 82. This allows for more precise determination of temperature of the return electrode pad 30 as opposed to a binary sensing system discussed above with respect to the switches 84. The change in status of the temperature sensing switches 84 and/or magnetic field measurements corresponding to temperature changes are transmitted to the generator 20, wherein appropriate actions are performed.

Figure 8C:
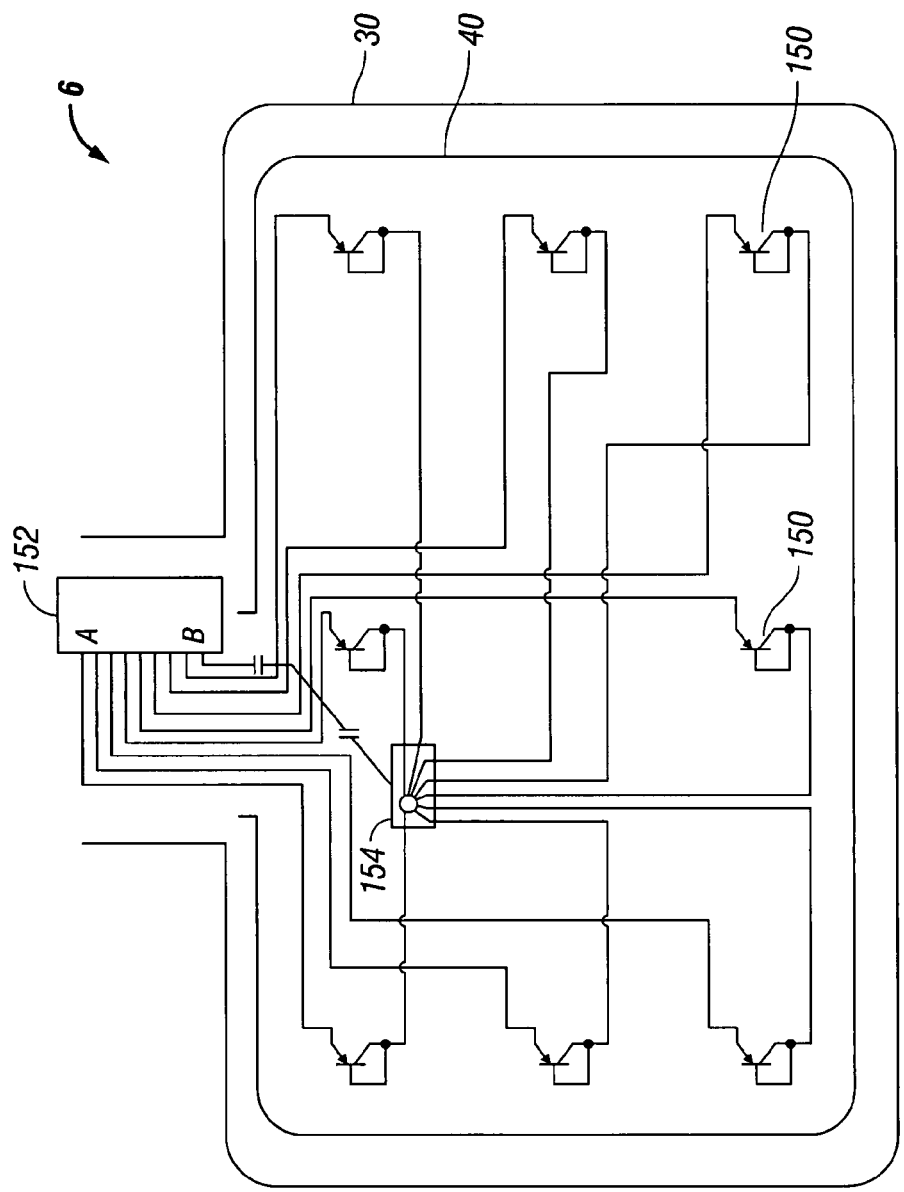

FIGS. 8A-C shows the return electrode 6 including a temperature sensing circuit 40 disposed therein. The temperature sensing circuit 40 includes one or more temperature sensor arrays 41 and 43 having at least one temperature sensor. Contemplated temperature sensors include thermocouples, thermistors, semiconductor (e.g., silicon) diodes, transistors, ferrite materials and Hall effect devices. The temperature sensing circuit 40 is disposed on a flex circuit (e.g., a flexible holding substrate 48) manufactured from suitable substrate, such as a polyimide film. Examples are films sold under the trademarks MYLAR™ and KAPTON™ and the like.

The diodes 42 are connected in series with one or more current limiting resistors 44 and are utilized as temperature sensors. The resistor 44 is coupled in series with the diode 42, having a resistance selected to set and limit the current flowing through the diode 42 at a predetermined level. The current flow to the diodes 42 is provided by a power source 50, such as a low voltage DC power source (e.g., battery, AC/DC transformer, etc.) connected in series with the diodes 42 and resistors 44 via interconnection wires 46. The power source 50 may be integrated into the generator 20 and draw power from the same source as the HVPS 27 (e.g., AC outlet). In one embodiment, interconnection of the diodes 42 and the resistors 44 is achieved by deposition of metal traces on the holding substrate 48 and soldering of the diodes 42 and the resistors 44 directly into the holding substrate 48. The holding substrate 48 may also electrically insulate the temperature sensing circuit 40 from the patient-contacting surface 32 to prevent RF energy being returned to the generator 20 from interfering with the circuit components.

The diodes 42 are so called "forward biased" such that current flows initially through the resistor 44 and from the diode's anode to the diode's cathode. In a forward biased diode 42, forward voltage drop (Vf) is produced that is in the range of about 0.5V to about 5V depending on the type of diode (e.g., light emitting diode). The forward voltage is directly dependent on the temperature. In particular, as the temperature increases, the semiconductor material within the diode 42 undergoes changes in their valence and conduction bands and consequently Vf decreases. Thus, by keeping the current flowing through the diode 42 constant via the resistor 44 and measuring the forward bias voltage allows for determination of the temperature of the diode 42.

The Vf signal is transmitted through the interconnection wires 46 to the generator 20, wherein the sensor circuit 22 analyzes the Vf to determine a corresponding temperature value. As those skilled in the art will appreciate, each of the interconnection wires 46 may include a corresponding isolation circuit (e.g., optical couplers) to translate electric signals (e.g., Vf) across isolation barriers, thereby isolating the temperature sensing circuit 40 from the RF supply.

The analysis process may include passing the Vf signals through an analog-to-digital converter and then multiplying the digitized Vf signal by a predetermined factor to arrive at a corresponding temperature value. The factor is derived empirically taking into consideration electrical properties of the diode 42, resistor 44 as well as electrical properties of the current being passed therethrough. The temperature signal is then transmitted to the controller 24 where it is further analyzed to determine appropriate action. For instance, comparing temperature measurements with a predetermined temperature threshold and adjusting or terminating the RF energy supply if the temperature measurement is larger than the predetermined threshold.

Temperature across the patient-contacting surface 32 may vary due to a number of factors (e.g., moisture content, adherence, etc.) affecting current density. Therefore, it may be desirable to measure temperatures at various points in the return electrode pad 30. Measuring temperature at various points allows for pinpointing the location of so-called "hot spots," segments of the patient-contacting surface 32 where current density exceeds that of the surrounding area and results in pad burn. Since measurement of Vf for each diode 42 provides for determination of corresponding temperature at the location of the diode 42, placing the diodes 42 strategically within the return electrode pad 30 allows for monitoring of temperature at those locations.

With reference to FIG. 8A, each resistor 44 and diode 42 pair is disposed within the conducting pad 30 such that the diode 42 provides temperature readings for a corresponding temperature monitoring zone 45. The size of the monitoring zone 45 depends on the distance between the diodes 42. The return electrode pad 30 may include any number of monitoring zones 45 of varying sizes. Each diode 42 is identified by the sensor circuit 22 as being associated with a particular monitoring zone 45 such that, when Vf signals are transmitted and subsequently converted into temperature readings, the generator 20 provides temperature monitoring for each of the monitoring zones 45. This data is utilized to instruct the user which specific portion of the return electrode pad 30 includes a hot spot so that preventative action may be taken, if necessary. This may include automatic RF supply termination and/or adjustment or manual termination of RF supply to ensure that the return electrode pad 30 adheres properly to the patient at the identified hot spot.

FIG. 8C shows another embodiment of return electrode 6 including a temperature sensing circuit 40 disposed on the return electrode pad 30. The temperature sensing circuit 40 includes one or more transistors 150, each of which is connected to a multiplexer 152. Similar to the diodes 42, the transistors 150 measure temperature as a function of the voltage drop which occurs as a result of temperature variation at the return electrode pad 30. The multiplexer 152 controls voltage flow to transistors 150, which in response to the voltage signal transmit a return voltage signal representative of the temperature of the return electrode pad 30. The transistors 150 are coupled to the multiplexer 152 via a bus 154. The voltage from the transistors 150 is then transmitted to the sensor circuitry 22 of the generator 20 which may be a temperature sensor.

Figure 9A:
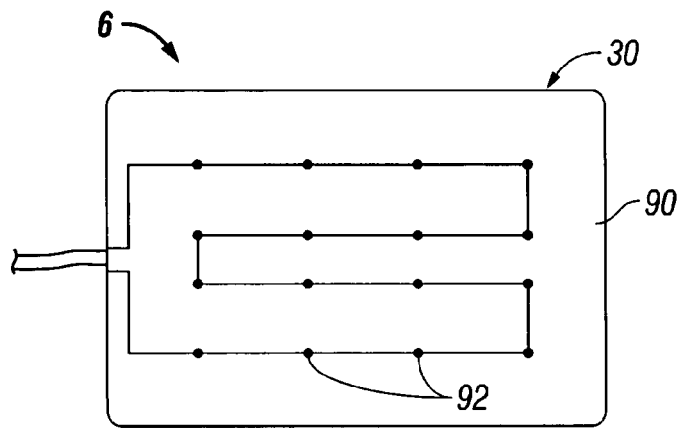
FIGS. 9A-B illustrate one embodiment of an electrosurgical return electrode having a temperature sensing circuit according to the present disclosure.
Figure 9B:
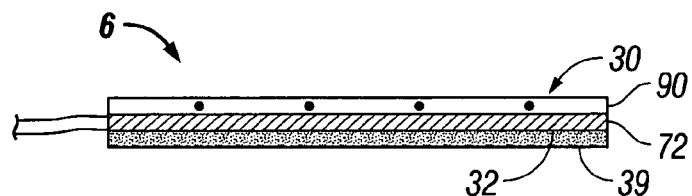

FIGS. 9A-B shows an embodiment of return electrode 6 that includes a temperature sensing circuit 90 disposed on top of the return electrode pad 30. The temperature sensing circuit 90 includes a plurality of switching elements 92 adapted to change impedance in response to temperature changes. One suitable type of switching elements 92 is a polymeric positive temperature coefficient overcurrent protection (PPTCOP) device, such as POLYSWITCH™, available from Raychem, a division of Tyco Electronics Corporation, located in Menlo Park, Calif. The switching elements 92 are wired in series and are disposed on a top surface of the return electrode pad 30 (e.g., on top of the foil layer 72).

The switching elements 92 may also be disposed on a suitable flex circuit (not explicitly shown), such as the flexible holding substrate 48 shown in FIG. 8B manufactured from a suitable substrate. The current flow to the switching elements 92 is provided by a power source (not explicitly shown), such as a low voltage DC power source (e.g., battery, AC/DC transformer, power source 50 of FIG. 8A etc.).

During operation, an interrogatory signal (e.g., from power source 50) is transmitted through the temperature sensing circuit 90 (e.g., interrogation current and/or voltage) to measure impedance and/or current of the switching elements 92. Measuring impedance of the temperature circuit 90 allows for determination of corresponding temperature of the return electrode pad 30. PPTCOP devices are configured to switch off, thereby increasing impedance, at different rates depending on the temperature. More specifically, at lower temperatures (e.g., about 40° C.) the PPTCOP devices turn off at a slower rate than at higher temperatures (e.g., about 45° C.). Therefore, duration of interrogation signals is adjusted to be of sufficient length to make sure that the sensor circuit 90 is interrogated properly. In other words, an interrogation signal at lower temperatures is longer since the activation time of the PPTCOP devices is slower than at higher temperatures, at which the interrogation signal is shorter.

The interrogation signal provides an interrogation circuit (e.g., generator 20) with the impedance measurement of the temperature sensing circuit 90. The generator 20 converts the impedance data to corresponding temperature data and if the temperature is above a predetermined threshold (e.g., 45° C.), the generator 20 performs one or more appropriate actions (e.g., issues an alarm).

Figure 10A:
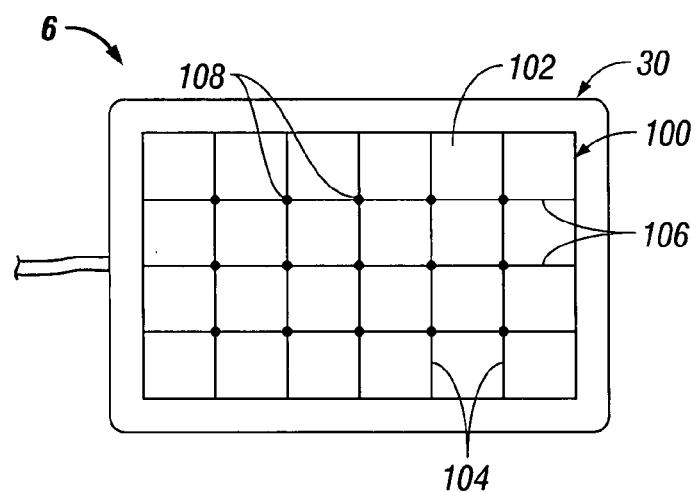
FIG. 10A-B illustrate one embodiment of an electrosurgical return electrode having a temperature sensing circuit according to the present disclosure.
Figure 10B:
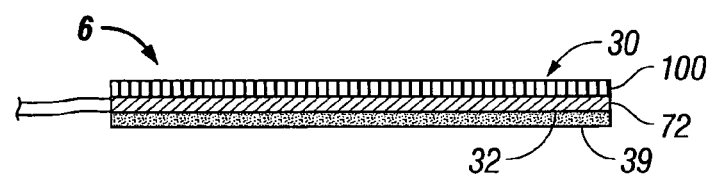

With reference to FIGS. 10A-B, another embodiment of the return electrode 6 having a temperature sensing circuit 100 disposed on top of the return electrode pad 30 is shown. The temperature sensing circuit 100 includes a thermocouple matrix 102 that allows for monitoring of temperature across an entire surface of the return electrode pad 30. The thermocouple matrix 102 includes a plurality of metallic filaments or wires disposed on top of the foil layer 72. More specifically, the thermocouple matrix 102 includes a first plurality wires 104 laid in a first direction across the top surface of the foil layer 72 and a second plurality of wires 106 laid in a second direction, which is substantially perpendicular to the first direction. The first plurality of wires 104 are made from copper and the like and the second plurality of wires 106 are made from constantan and the like. Each of the first plurality of wires 104 intersects with each of the second of plurality of wires 106 at a plurality of junctions 108 thereby forming the thermocouple matrix 102. The junction 108 of first and second plurality of wires 104 and 106 create a so-called "Seebeck effect." The voltage produced at the junction 108 of two dissimilar metals changes directly with temperature. Different wire type are chosen based on the metal's ability to form different thermocouple junctions which are known to exhibit a given voltage at a given temperature. Following combination of wires as shown in Table 1 may be used.

TABLE 1

|  | TYPE E | TYPE J | TYPE K | TYPE R | TYPE S | TYPE T |
| --- | --- | --- | --- | --- | --- | --- |
| First wires | 10% Nickel Chromium | Iron | 10% Nickel Chromium | 13% Platinum Rhodium | 10% Platinum Rhodium | Copper |
| Second wires | Constantan | Constantan | 5% Nickel Aluminum Silicon | Platinum | Platinum | Constantan |

As appreciated by those skilled in the art, the junctions 108 represent the so-called "hot junctions," which allow for relative temperature measurement of the return electrode pad 30 since each of the "hot junctions" are operatively connected to a "cold junction" (not explicitly shown). During operation, a voltage is passed to each of the junctions 108. Each junction 108 is interrogated individually, wherein the switching of the interrogation signal is performed by a suitable multiplexer (not explicitly shown) or a similar device. The interrogatory polling may be performed in a serial fashion and the polling data is sent to the generator 20 or a control circuit disposed directly within the return electrode pad 30 as shown in FIG. 11 and discussed in more detail below.

A signal processor monitors the polling data for the junction 108 having the highest temperature. Thereafter, the temperature of the warmest junction 108 is compared with the maximum safe temperature, which is from about 40° to about 45° C. Those skilled in the art will appreciate that if the return electrode pad is of resistive type, heating thereof is more uneven than heating of capacitive type electrode pad. Therefore, spacing between junctions 108 is adjusted to accommodate various types of return electrode pads.

Figure 11:
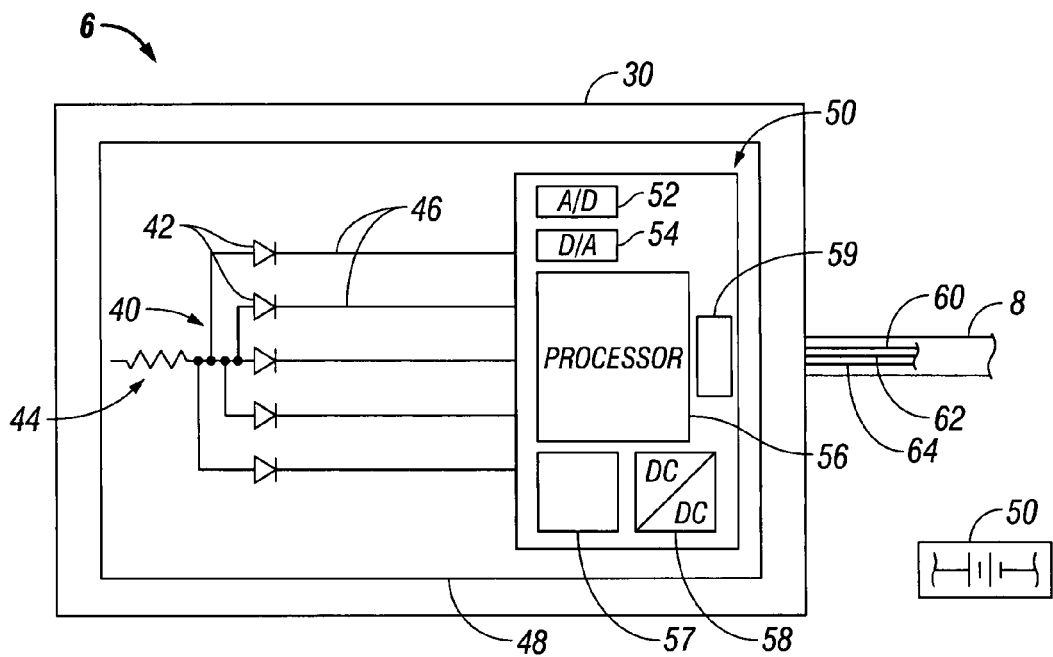
FIG. 11 is a cross-sectional plan view of a smart electrosurgical return electrode having temperature sensing circuit according to the present disclosure.

FIG. 11 shows another embodiment of the return electrode pad 30 that includes a control circuit 51 disposed on flexible holding substrate 48. The control circuit 51 is coupled to the temperature sensing circuits disclosed in the above embodiments (e.g., temperature sensing circuits 40, 90 and 100) and is configured to receive sensor signals therefrom. Other sensor circuits may be used in conjunction with the control circuit 51 and the discussion of the temperature sensing circuit 40 represents one embodiment of the present disclosure.

In particular, the control circuit 51 analyzes the sensor signals and performs similar functions as the sensor circuit 22. Since processing of sensor signals occurs at the return electrode pad 30 this obviates the need for running the interconnection wires 46 directly to the sensor circuit 22. Consequently, isolation circuits for each of the interconnection wires 46 are also no longer necessary. Placement of the control circuit 51 at the return electrode pad 30 also provides a reduction in amount of circuit components necessary for the generator 20 and reduces high frequency leakage-to-earth referenced circuits.

The control circuit 51 includes an analog-to-digital converter 52, a digital-to-analog converter 54, a microprocessor 56, a DC-DC converter 58, a serial transceiver 57, and an optical coupler 59. Those skilled in the art will appreciate that the control circuit 51 may include additional circuit components, such as clocks, microcontrollers, cold junction compensation with thermistor, resistors, capacitors, oscillators, field-programmable gate arrays, etc. The circuit components of the control circuit 51 are electrically insulated from the patient-contacting surface 32 via the substrate 48. Further, since the holding substrate 48 includes metal traces deposited thereon, the circuit components are bonded directly thereto and holding substrate acts as an electrical interconnect between the circuit components.

The control circuit 51 and the temperature sensing circuit 40 are powered by the power source 50, which is coupled thereto via a power line 60. The power line 60 includes one or more wires adapted to transmit lower voltage DC current. The DC-DC converter 58 adjusts the power from the power source 50 to suit the circuit components of the control circuit 51 and the temperature sensing circuit 40.

The temperature sensing circuits 40, 90 and 100 transmit corresponding voltage, current and/or impedance signals through the interconnection wires 46 to the control circuit 51. The control circuit 51 analyzes the sensor signals to determine a corresponding temperature value. The sensor signals are initially passed through the A/D converter 52. Thereafter, the digitized sensor signals are analyzed by the microprocessor 56 (e.g., multiplying the digitized sensor signal by a predetermined factor to arrive at a corresponding temperature value) to obtained processed data (e.g., temperature values). Those skilled in the art will understand that additional logic circuits may be included in the control circuit 51, such as microcontrollers and field-programmable gate arrays, depending on the complexity of computations being performed.

The processed data is transmitted to the generator 20 for further analysis via a data line 62. Prior to transmission, the temperature signals may be converted to analog signals for transmission via a serial data transfer protocol. This is accomplished via the D/A converter 54. The serial transceiver 57 (e.g., universal asynchronous receiver/transmitter) establishes serial communications with its counterpart transceiver at the generator 20 and transmits the individual bits of processed data in a sequential fashion. The signals carrying the processed data are passed through the optical coupler 59 which is connected to the data line 62. The optical coupler 59 isolates the control circuit 51 from the RF supply by transmitting the signals across an isolation barrier. It is envisioned that the optical data transmission methods utilizing fiber optics may be used in place of the data line 62 to transfer data to the generator 20 from the control circuit 51. This eliminates electrical interference and RF leakage. The RF energy is returned to the generator 20 via a return line 64. The power line 60, the data line 62 and the return line 64 are enclosed within the cable 8.

In embodiments, the analog sensor signals from the temperature circuits 40, 90 and 100 may be transmitted to an analog MUX which is coupled to a counter (not explicitly shown). These circuit components are configured to measure the voltage signal corresponding to the temperature readings and transmit the processed data to the generator 20. Further, with reference to the embodiment of temperature sensing circuit 100 shown in FIGS. 10A-B, the multiplexer or similar device suitable for rapid switching of interrogatory signals of the thermocouple matrix 102, may also be incorporated into the control circuit 51.

At the generator 20, the processed data is then transmitted to the controller 24 where it is further analyzed to determine appropriate action. For instance, comparing temperature measurements with a predetermined temperature threshold and adjusting or terminating the RF energy supply if the temperature measurement is larger than the threshold.

Figure 12:
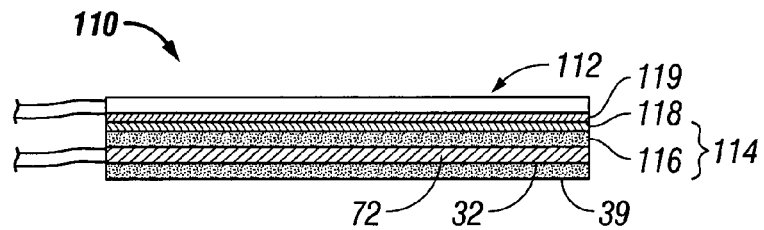
FIG. 12 is a cross-sectional side view of a modular electrosurgical return electrode according to the present disclosure.

The circuit components of the present disclosure are integrated directly into the return electrode pad 30. To minimize the cost of these pads, it is desirable to make the return electrode modular, wherein the circuit components are reused from one procedure to the next. FIG. 12 shows a cross-sectional side view of a modular return electrode pad 110 which includes the circuit components (e.g., control circuit 51, temperature sensing circuits 40, 90 and 100, etc.) disposed on a detachable substrate 112. The detachable substrate 112 is configured to temporarily attach to disposable portion 114 (shown in assembled configuration in FIG. 12). More specifically, the disposable portion 114 includes the foil layer 72 with the adhesive material layer 39 disposed on the bottom surface thereof. A second adhesive material layer 116 is disposed on the top surface of the foil layer 72. The second adhesive material layer 116 is used to bond a removable release liner 118, which secures the detachable substrate to the disposable portion 114. Further, the second adhesive material layer 116 also acts as a heat conductor.

The detachable substrate 112 includes an insulative material layer 119 at the bottom surface thereof and the bottom surface of the insulative material layer 119 is configured to selectively attach to the removable release liner 118. The insulative material layer 119 may be formed from polyolefin, Mylar or other similar dielectric materials. During operation, the release liner 118 is removed exposing the adhesive material layer 116 and the detachable substrate 112 is attached to the disposable portion 114 via the insulative material layer 119 and the adhesive material layer 116. This configuration allows for the detachable substrate 112 to be temporarily attached to the disposable portion 114 during electrosurgical procedures. Once the procedure is complete, the detachable substrate 112 is separated from the disposable portion 114.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical return electrode, comprising:
    a conductive pad including a patient-contacting surface configured to conduct electrosurgical energy; and
    a temperature sensing circuit coupled to the conductive pad, the temperature sensing circuit including a plurality of switching elements electrically connected in series, wherein each of the plurality of switching elements is a polymeric positive temperature coefficient overcurrent protection device configured to vary in impedance in response to temperatures changes, the temperature sensing circuit configured to receive an interrogation signal serially transmitted therethrough by a low voltage DC power source to measure an overall impedance value of the plurality of switching elements, wherein the measured impedance is indicative of the temperature changes.

2. An electrosurgical return electrode according to claim 1, wherein the temperature sensing circuit is a flexible circuit.

3. An electrosurgical return electrode according to claim 1, wherein each of the plurality of switching elements is configured to switch off to allow for increased impedance at different rates based on temperature.

4. An electrosurgical return electrode according to claim 3, wherein each of the plurality of switching elements switches off at (i) a first rate at a temperature of about 40° C. and (ii) at a second rate at a temperature of about 45° C., the first rate being less than the second rate.

* * * * *